United States Patent [19]

Lanam et al.

[11] Patent Number: 4,608,229

[45] Date of Patent: Aug. 26, 1986

[54] PALLADIUM METAL BASE DENTAL ALLOY

[75] Inventors: Richard D. Lanam, Westfield; Allen R. Robertson, Edison, both of N.J.

[73] Assignee: Engelhard Corporation, Menlo Park, N.J.

[21] Appl. No.: 649,468

[22] Filed: Sep. 12, 1984

[51] Int. Cl.$^4$ .................................................. C22C 5/04
[52] U.S. Cl. ..................................... 420/464; 433/207
[58] Field of Search ................ 420/464; 433/200, 207

[56] References Cited

U.S. PATENT DOCUMENTS

| | | | |
|---|---|---|---|
| 4,387,072 | 6/1983 | Schaffer | 420/464 |
| 4,400,350 | 8/1983 | Wagner | 420/464 |
| 4,419,325 | 12/1983 | Prasad | 420/464 |
| 4,451,639 | 5/1984 | Prasad | 420/464 |
| 4,518,564 | 5/1985 | Prasad | 420/464 |
| 4,551,302 | 11/1985 | Wagner et al. | 420/464 |

FOREIGN PATENT DOCUMENTS

| | | | |
|---|---|---|---|
| 3239338 | 2/1984 | Fed. Rep. of Germany | 420/464 |
| 3247398 | 7/1984 | Fed. Rep. of Germany | 420/464 |

*Primary Examiner*—L. Dewayne Rutledge
*Assistant Examiner*—Robert L. McDowell
*Attorney, Agent, or Firm*—Inez L. Moselle

[57] ABSTRACT

A palladium alloy for use in making porcelain jacketed dental restorations having the following composition: 60-85 percent by weight palladium, 5-20 percent by weight copper, 3-15 percent by weight gallium, and a modifier metal selected from gold, indium, ruthenium, tin, nickel and mixtures thereof, the sum of the concentrations of the modifier metal percent in the alloy being greater than 5.5 percent by weight.

6 Claims, No Drawings

PALLADIUM METAL BASE DENTAL ALLOY

The present invention relates to a palladium metal base alloy especially adapted for use in the dental field for the prepartion of caps, crowns, inlays and other dental prosthesis to which it is desired to apply porcelain or other like ceramic surface to reproduce the function, color and shape of natural teeth.

In the dental field, one of the most sought after alloys is one to which porcelain can be applied by fusion and which will have complete adhesion throughout the temperature range and other conditions to which the alloy and porcelain will be subjected to during processing and use.

Until recent years, gold alloys, usually gold/platinum alloys have been used as dental alloys. As gold prices have climbed, researchers and practioners have sought alternatives to gold. Such alternatives must provide alloys which are low in cost, easy to fabricate and which are compatible with and bond strongly to porcelain formulations used in dental prostheses. One approach has been to lower the gold content and add more palladium to the alloy. For example, U.S. Pat. No. 4,387,072 is directed to dental casting alloys in which palladium is the major constituent and represents one effort in an attempt to substitute lower cost metals for gold in dental casting alloys. The dental casting alloy disclosed and claimed in the patent consists of the following composition:

|  | % by weight |
| --- | --- |
| Metal Component | |
| Pd | 50-85 |
| Cu, Co | 5-40 |
| Ga | 1-15 |
| Modifier metals | |
| Ni, Au, In, Ru, Sn | 5% Max. |
| B | 1% Max. |
| Grain refiner metal Rh, Ir | 0.5% Max. |

The modifier metals are incorporated in the palladium base alloy to prevent discoloration of dental porcelations during the firing step of the porcelain casting on the palladium casting. U.S. Pat. No. 4,387,072 advises the art that amounts of the modifier metal in excess of 3.0% by weight provide no additional benefit and cautions the art not to employ amounts in excess of 5% by weight as such excess amounts "adversely affect the balance of properties of the alloy."

It has unexpectedly been discovered, that contrary to the teachings of U.S. Pat. No. 4,387,072, when selected modifier metals such as gold, indium and ruthenium are incorporated in palladium alloys containing copper and gallium the modifier metals being present in amounts in excess of 5% by weight, there is obtained a low cost dental alloy casting having a fracture-resistant, non-dentritic structure with acceptable Vickers Hardness and exhibiting improved ductility and excellent porcelain bond strength.

Specifically the dental casting alloys of the present invention have the following composition:

|  | % by weight |
| --- | --- |
| Metal Component | |
| Pd | 60-85 |
| Cu | 5-20 |
| Ga | 3-15 |
| Modifier Metal | |
| Au | 0.5-2 |
| In | 3 2-6 |
| Ru | 0.005-0.02 |
| Sn | 0-2 |
| Ni | 0-2 | the sum of the concentrations of the modifier metals present in the palladium base dental alloy being greater than 5.5% by weight.

DETAILED DESCRIPTION OF THE INVENTION

The palladium alloys of the present invention are useful in dental restorations and do not discolor porcelain and remain ductile after firing of a porcelain jacket or coating on them. Upon solidification from the melt the cast alloy consists of a single phase solid solution microstructure free of dendritic grain structure whereby the casting is substantially fracture resistant. Porcelain jacketed dental restorations exhibit excellent bond strength between the porcelain coating and the underlying alloy.

As hereinafter more specifically indicated, the alloys of the present invention use palladium as the principal component, and use copper, gallium as otherr essential components, gold, indium, ruthenium as modifier components. Nickel and tin may also be optionally be present in minor amounts as modifier components.

The alloys of the present invention must contain at least about 60 percent palladium and may contain as much as 85 percent by weight palladium. Preferably the alloy contains about 70 to about 80 percent by weight palladium to obtain the desired nobility and an optimum balance of properties.

The inclusion of the alloying metals of copper, gallium, gold, indium, ruthenium, tin and nickel have individual effects on the alloy which render the cast alloy of the present invention useful in the fabrication of dental restorations in which the cast alloy is covered with a porcelain or other ceramic coating or jacket.

The inclusion of gold in the alloy increases ductility and malleability of the alloy. In the palladium base alloy of the present invention, gold is present at a concentration range of about 0.5 to about 2 percent by weight and preferably at a concentration range of about 1.5 to about 1.9 percent by weight.

Copper is a low cost filler metal which is compatible with palladium and functions in combination with gallium to form oxides when cast which promote bonding of porcelain coatings to the cast alloy. Copper is present in the alloy of the present invention at a concentration range of about 5 to about 20 percent by weight and preferably about 8 to about 12 percent by weight and most preferably about 10 percent by weight. Gallium is present in the palladium base alloy of the present invention at a concentration range of about 3 percent to about 15 percent by weight, preferably about 5 to about 9 percent by weight and most preferably about 7 percent by weight.

The presence of indium in the palladium alloy of the present invention also promotes bonding with porcelain coatings fired on the alloy casting. Indium is present in the palladium alloy at concentration ranges of about 3.2 to about 6 percent by weight and preferably about 4.5 to about 5.5 percent by weight.

Ruthenium is incorporated in relatively minor amounts in the palladium alloy and functions as a grain refiner to promote reduced, uniform grain size in structures cast from the alloy. Ruthenium is present in the palladium alloy at a concentration range of about 0.005 to about 0.02 percent by weight and preferably about 0.006 to about 0.012 percent by weight. As hereinbefore indicated, nickel and tin are optionally included in the palladium alloy of the present invention. Nickel may be present in the alloy at a concentration range of from 0 to about 2 percent by weight and preferably about 0.8 to about 1.2 percent by weight. Nickel when included in the alloy composition aids in eliminating internal oxides. Tin when included in the alloy also effects oxide formation and may be used at a concentration range of about 0 to about 2 percent by weight and preferably about 0.8 to about 1.2 percent by weight.

The modifier metals, gold, indium, ruthenium, tin and nickel incorporated in the palladium base alloy compositions of the present invention are present at concentrations greater than 5 percent by weight namely, 5.5 percent by weight or more, desirably at a concentration range of about 5.5 percent by weight to about 8.5 percent by weight and preferably about 6.5 to about 7.5 percent by weight. When present in the alloy at these concentrations, the modifier metals unexpectedly effect an improvement in bond strength between porcelain coatings fired against castings prepared from the alloy.

The components are alloyed by melting the metal components in a vacuum furnace and then casting the melt into ingots. Conventional techniques are used to make a finished dental restoration with the alloy. An investment mold is prepared by using the coventional lost-wax process. The alloy is then melted and poured in the mold which is mounted in a centrifugal casting machine. After cooling, the mold is broken away and the casting cleaned, polished, and finished in preparation for application of dental porcelains by the usual firing techniques.

As will hereinafter be illustrated, improved adhesion results are obtained when the alloy is bonded to dental porcelains available on the commercial market such as porcelain materials available from Vita Zahnfabrik under the trademark VMK-68, porcelain materials from the Howmedica Corporation or the Ceramco Division of Johnson & Johnson.

Dental restorations obtained by firing of a porcelain jacket thereon exhibit a Vickers Hardness of about 230-250 which is substantially above the minimum Vicker Hardness of 150 required for dental restorations to withstand mastication abrasion. The palladium base alloy of the present invention has a solidus temperature in excess of 1100° C. so that the alloy and porcelain can be fired with standard equipment found in dental laboratories. The alloy has a relatively high coefficient of thermal expansion, namely about 0.688% at 500° C. which renders the alloy compatible with most commercial porcelains.

The following example is given to illustrate certain preferred details of the invention, it being understood that the details of the example are not to be taken as in any way limiting the invention thereto.

EXAMPLE

A palladium alloy of the present invention designated "Alloy A" having a combined modifier metal concentration of 6.81 percent by weight was prepared. Alloy A had the following composition:

|  | % by Weight |
|---|---|
| Metal |  |
| Pd | 76.19 |
| Cu | 10.00 |
| Ga | 7.00 |
| Modifiers |  |
| In | 5.00 |
| Au | 1.80 |
| Ru | 0.01 |

For purposes of comparision, a second palladium alloy, designated "Alloy B" of the type disclosed in U.S. 4,387,072 was prepared having a combined modifier metal concentration of 1.81 percent by weight. The comparative Alloy B had the following composition:

|  | % by weight |
|---|---|
| Metal |  |
| Pd | 77.80 |
| Cu | 10.00 |
| Ga | 10.39 |
| Modifiers |  |
| In | — |
| Au | 1.80 |
| Ru | 0.01 |

To prepare the alloys, the ingredients were mixed together and melted in a furnace at 1260° C. The melted alloys were then cast into bar molds to prepare specimens for determining the tensile properties of the alloys. A first set of cast alloys was allowed to bench cool for 60 minutes before the specimens were divested from the molds. A second set was subjected to water quenching to provide annealed specimens. The tensile properties of Alloys A and B were determined using an Instron tensile tester and are summarized in Table I below.

TABLE I

| TENSILE PROPERTIES | | | | |
|---|---|---|---|---|
|  | Alloy A | | Alloy B | |
|  | As Cast | Annealed | As Cast | Annealed |
| Tensile Strength, Psi | 158,760 | 136,124 | 164,410 | 155,314 |
| Yield Strength, Psi | 75,039 | 64,495 | 102,499 | 79,499 |
| Elongation, % | 16.0 | 26.0 | 14.5 | 26.0 |

The data recorded in Table I indicate that the tensile properties of Alloy A are adequate for use in dental restorations. Although the tensile and yield strengths of Alloy A are less than Alloy B, Alloy A is more ductile and therefore more easily workable than Alloy B, workability being a desirable property in the fabrication of dental restorations requiring grinding and burnishing to provide an appropriate finish.

The thermal expansion of the two alloys which is substantially equivalent is recorded in Table II below:

TABLE II

| Alloy | Thermal Expansion % at 55° C. |
|---|---|
| A | 0.668 |
| B | 0.676 |

Grain size and Vickers Hardness of the Alloys A and B was determined by casting rings at 1260° C. from ingots prepared from alloys A and B whereupon the cast rings were either allowed to bench cool for 20 minutes before divesting from the mold or the cast ring was bench cooled for 5 minutes and then quenched in room temperature (74° F.) water. Copings cut from the bench cooled as well as water quenched rings were simultaneously put through six firing cycles as follows:

1. Degass/Oxidizing Cycle

Coping placed in furance at 1200° F. and the furnace temperature raised to 1850° F. in air and held thereat for 10 minutes, whereupon the coping was removed from the furance and placed under a beaker to cool slowly.

2. Opaque Cycle - Two Coats, Repeated Twice

The cooled degassed coping from (1) was placed in a furance and the furnace temperature raised to 1800° F. under vacuum and held thereat for 30 seconds whereupon the vacuum was released, the coping removed from the furnace and slowly cooled under a glass beadker.

3. Body Bisque Bake Cycle - Two Layers, Repeated Twice

The coping treated in (2) was placed in a furnace at 1200° F. and heated to 1760° F. under vacuum and held thereat for 30 seconds, whereupon the vacuum was released, the coping removed from the furnace and slowly cooled under a glass beaker.

4. Glaze Bake Cycle

The coping treated in (3) was placed in a furnace at 1200° F. And heated to 1700° F. in air and held thereat for 30 seconds, whereupon the coping was removed from the furnace and slowly cooled under a glass beaker.

Photomicrographs (100x) were taken of crosssections cut from uncast ingot buttons taken from the mold after casting of the ingots as well as the unfired and porcelain fired copings. By examination of the photomicrographs, the grain structure of the various alloy specimens was determined and are recorded in Table III below.

Recorded in Table IV below is the Vicker Hardness of the various specimens. Vickers Hardness was obtained by testing specimens of the alloy with a microhardness tester with a diamond indenter.

TABLE III

| | Grain Size of Alloy | | | | | |
| | Before Casting Alloy | | Bench Cooled Alloy | | Quenched Alloy | |
| Specimen | A | B | A | B | A | B |
| --- | --- | --- | --- | --- | --- | --- |
| Ingot | #1 | #10 | — | — | — | — |
| Button | — | — | #5½ | Den.* | #6 | Den. |
| Unfired Coping | — | — | #3 | Den. #0.0 | #3 | Den. |
| Fired Coping | — | — | #3 | Den. | #3½ | Den. |

*Den = dendritic

With respect to the data recorded in Table III, grain size was measured on a scale of from #0.0 to #10.0. The larger the number, the finer the grain size. A grain size of #0.0 is equivalent to 406 microns average grain diameter. A grain size of #5 is equivalent to 79 microns and a grain size of #10 is equivalent to 18 microns.

The data recorded in Table III indicate that the castings prepared from Alloy A have a homogeneous single phase solid solution microstructure of midsized grain structure whereas Alloy B has a consistent dendritic, non-homogeneous two-phase solid solution microstructure which indicates that the alloy is brittle and susceptible to fracturing or chipping when impacted.

TABLE IV

| | VICKERS HARDNESS | | | | | |
| | Before Casting Alloy | | Bench Cooled Alloy | | Quenched Alloy | |
| Specimen | A | B | A | B | A | B |
| --- | --- | --- | --- | --- | --- | --- |
| Ingot | 314.5 | 346.5 | — | — | — | — |
| Button | — | — | 235.3 | 320.2 | 249.5 | 295.0 |
| Unfired Coping | — | — | 250.5 | 386 | 255.0 | 360 |
| Fired Coping | — | — | 235.2 | 324.0 | 253.0 | 304.5 |

The data in Table IV indicate that although castings prepared from the palladium alloy of the present invention (Alloy A) have a Vickers Hardness less than castings prepared from alloys of the prior art (Alloy B) and are therefore somewhat softer than castings prepared from the alloy of the present invention, Alloy A exhibits a Vickers Hardness sufficient to meet the requirements for dental restorations, i.e., a Vickers Hardness in excess of 150.

Test flags 30 mm×10 mm×0.5 mm prepared from castings of Alloy A and fired with several different commercial dental porcelains were tested for bond strength of the fired porcelain to the casting in accordance with a Flexure Adhesion Test which approximates the ability of the porcelain coated casting to withstand the stresses and strains of mastication using an Instron test machine at a cross-head rate of 0.05 in/min. The test procedure consisted of continuous loading until a perturbation of the load-deflection curve, which was indicative of bond failure occurred. Each test was replicated 6 times. With respect to the test results, the higher the applied load (in pounds) the stronger is the bond between the fired porcelain and the casting. The bond strength test results are recorded in Table V below and each recorded test result represents the average of 6 tests. For comparative purposes, test flags were also prepared from the commercial porcelains fired against the castings of Alloy B. The bond strength results for the porcelains fired on Alloy B castings are also recorded in Table V below.

TABLE V

| FLEXURE ADHESION OF PORCELAIN TO CASTING | | | |
| | Bond Strength (lbs.) Commercial Porcelain | | |
| Alloy | Ceramco | VMK-68 | Howmedica |
| --- | --- | --- | --- |
| A | 5.20 | 4.40 | 5.50 |
| B | 4.24 | 3.53 | 3.03 |

By reference to the data in Table V, it is immediately apparent that the bond strength of commercial porcelains to castings prepared from alloy formulations of the present invention (Alloy A) is consistently greater than the bond strength of commercial porcelains to castings prepared from Alloy formulations of the prior art (Alloy B).

While specific components of the present system are defined above, many other variables may be introduced which may in any way affect, enhance or other wise improve the system of the present invention. These are intended to be included herein.

Although variations are shown in the present application, many modifications and ramifications will occur to those skilled in the art upon a reading of the present disclosure. These, too, are intended to be included herein.

We claim:

1. A castable dental alloy composition suitable for bonding with dental porcelain consisting essentially of about 60 to 85 percent by weight palladium, about 5 to 20 percent by weight copper, about 3 to about 15 percent by weight gallium, about 0.5 to about 2 percent by weight gold, about 3.2 to about 6 percent by weight indium, about 0.005 to about 0.02 percent by weight ruthenium, 0 to about 2 percent by weight tin and 0 to about 2 percent by weight nickel, wherein the sum of the concentrations of gold, indium, ruthenium, tin and nickel present in the alloy ranges from greater than 5.5 percent by weight to about 8.5 percent by weight.

2. The alloy defined in claim 1 formed as a cast body for use as a dental prosthesis and further comprising a porcelain jacket fired on the body.

3. A dental composition consisting essentially of about 70 to about 80 percent by weightt palladium, about 8 to 12 percent by weight copper, about 5 to 9 percent by weight gallium, about 1.5 to 1.9 percent by weight gold, about 4.5 to about 5.5 percent by weight indium, 0 to about 2 weight percent tin, 0 to about 2 percent by weight nickel and about 0.006 to about 0.012 percent by weight ruthenium, the sum of the concentrations of gold, indium, ruthenium, tin and nickel present in the alloy composition ranging from greater than 5.5 percent by weight to about 8.5 percent by weight.

4. The alloy defined in claim 3, formed as a cast body for use as a dental prosthesis and further comprising a porcelain jacket fired on the body.

5. The alloy defined in claim 4 formed as a cast body for use as a dental prosthesis and further comprising a porcelain jacket fired on the body.

6. A dental alloy composition consisting essentially of about 70 to about 80 percent by weight palladium, about 8 to about 12 percent by weight copper, about 5 to about 9 percent by weight gallium, about 0.5 to about 2 percent by weight gold, about 3.2 to about 6 percent by weight indium, 0 to about 2 percent by weight tin, 0 to about 2 percent by weight nickel, and about 0.005 to about 0.02 percent by weight ruthenium, wherein the sum of the concentrations of gold, indium and ruthenium in the alloy composition ranges from greater than 5.5 percent by weight to about 8.5 percent by weight.

* * * * *